United States Patent [19]

Stockum

[11] Patent Number: 4,853,978

[45] Date of Patent: Aug. 8, 1989

[54] ANTIMICROBIAL MEDICAL GLOVE

[75] Inventor: Glenn F. Stockum, Arlington, Tex.

[73] Assignee: Surgikos, Inc., Arlington, Tex.

[21] Appl. No.: 77,543

[22] Filed: Jul. 24, 1987

[51] Int. Cl.⁴ .................. A41D 19/00; A61M 35/00
[52] U.S. Cl. .................................... 2/167; 604/292
[58] Field of Search ......................... 2/167; 604/292

[56] References Cited

U.S. PATENT DOCUMENTS

| | | | |
|---|---|---|---|
| 3,347,233 | 10/1967 | Migliarese | 128/260 |
| 3,384,083 | 5/1968 | Cozza et al. | 128/260 |
| 3,662,054 | 5/1972 | Wollmann et al. | 2/167 X |
| 3,896,807 | 7/1975 | Buchalter | 128/261 |
| 4,381,380 | 4/1983 | LeVeen et al. | 604/265 X |
| 4,567,065 | 1/1986 | Schneiderman | 427/230 |

*Primary Examiner*—David Werner
*Attorney, Agent, or Firm*—Charles J. Metz

[57] ABSTRACT

An antimicrobial medical glove consisting essentially of an outer elastomeric body in the shape of a hand and an inner coating containing an antimicrobial agent, said inner coating being capable of slowly releasing said antimicrobial agent in an amount and over a period of time sufficient to maintain an essentially bacteria-free and fungus-free environment within said glove after said glove has been donned.

4 Claims, No Drawings

ANTIMICROBIAL MEDICAL GLOVE

The invention relates to a medical glove such as a surgeon's or examination glove which contains an antimicrobial inner layer.

BACKGROUND OF THE INVENTION

Typically, several steps are required to insure that surgeon's gloves are free of bacteria or other microorganisms during surgery. Prior to donning the gloves, the surgeon must scrub his hands thoroughly with a strong bactericidal soap and a brush or sponge in an attempt to eliminate or drastically reduce inimical microorganisms from his hands. Using sterile techniques, he dons surgeon's gloves which have been presterilized in the package. Assuming the steps are strictly adhered to, the surgeon's gloves do not convey bacteria into the wound site. However, after the most rigorously maintained sequence of scrubbing and proper donning, the surgeon's hand quickly becomes covered with bacteria inside of the sterile gloves. The bacteria are present deep in the pores of the skin and cannot be removed by scrubbing. After the hands are scrubbed and gloves are donned, bacteria percolate out of the pores and quickly reinfest the hands. Although these bacteria seldom present any hazard to the surgeon, they can create a hazard to the patient being operated on if the integrity of the glove is compromised. Sometimes the gloves will have a pinhole from time of manufacture, or the gloves are snagged during donning, or the gloves are punctured by an instrument or a bone fragment. Because the hands perspire inside the gloves, a reservoir of bacteria laden liquid is usually present and is easily transferred through any rupture of the rubber film into the wound site. Conversely, infected fluids from the patient can transfer through a damaged glove onto the surgeon's hands.

Strong germicides cannot be residual on the hands when the gloves are donned because they often irritate or sensitize the surgeon's hands.

SUMMARY OF THE INVENTION

The invention provides a medical glove comprising an outer elastomeric body in the shape of a hand, said glove having an inner coating that contains an antimicrobial agent, said inner coating being capable of slowly releasing said antimicrobial agent in an amount and over a period of time sufficient to maintain an essentially germ-free bacteria-free and fungus-free environment within said glove after the glove has been donned.

A principal object of the invention is to provide a surgical glove which provides greater safety to the patient and to the surgeon than contemporary gloves.

The surgeon's glove of the invention comprises an outer glove body, as worn, with an inner layer containing an antimicrobial material.

A feature of the antimicrobial containing inner layer is the permeability of the layer to perspiration to allow transport of the antimicrobial to microbes on the hand.

Another feature of the bound antimicrobial is the lower tendency to sensitize or irritate the hands as a result of slow migration of the active agent from the inner layer to the hand.

Another feature of the antimicrobial containing inner layer is one of economics. The active agents are expensive, and because the inner layer is a minor portion of the glove, the glove of this invention is more economical than it would be if the active agents were incorporated in the entire glove.

A further feature of the invention is the option of allowing the antimicrobial to be applied to the inside of the glove or to both the inside and the outside of the glove.

THE PRIOR ART

Gloves have been employed as carriers to dispense or administer medicaments or cosmetic agents to the skin of the wearer. The following U.S. Patents are typical of such disclosures:

| | |
|---|---|
| Schneiderman | No. 4,567,065 |
| Buchalter | No. 3,896,807 |
| Cozza et al. | No. 3,384,083 |
| Migliarese | No. 3,347,233 |

These disclosures differ in principle from this invention in that it is not the purpose of the gloves of this invention to serve as a means for administering a medically active agent to the wearer. Rather, it is the intent of this invention to provide a means for maintaining, as far as is practical, the sterility of a surgeon's glove by providing small amounts of an antimicrobial agent to the hand/glove interface.

DETAILED DESCRIPTION OF THE INVENTION

As used herein, "antimicrobial" refers to a composition having fungicidal, bactericidal, and/or bacteriostatic properties.

Natural rubber surgical gloves are commonly produced by employing a dip process. Glazed or bisque porcelain or plastic molds in a configuration duplicating the human hand are dipped into compounded natural rubber latex to result in a thin rubber glove. To establish a predictable, reproducible rubber layer on the molds, a coagulant layer is first dipped onto the clean molds. These coagulant coated molds are dipped into the latex compound, which gels into a layer. The rubber gel is leached in water to extract a large percentage of the soluble components of the compound. After leaching, the gloves are dried and cured.

The finished rubber gloves would have too much surface tack to allow removal from the molds without ancillary treatments or additives to the process. A common approach utilizes inert or nontoxic powders in the coagulant and in a post-dip applied after the gloves are dried and cured. A common powder that is suspended in the coagulant is calcium carbonate. The calcium carbonate isolates the rubber film from the mold, facilitating removal of the finished gloves. It also becomes a residual antiblocking agent on the exterior surface of the finished gloves. The powder applied after the glove is cured is commonly epichlorohydrin cross-linked cornstarch which becomes an antiblock and donning assist on the inside of the finished gloves. Both of the aforementioned powders are believed to be bioabsorbable if left in a wound site.

Some of the antimicrobials employed in the invention have an affinity for the aforementioned cross-linked cornstarch. Because of this trait, excellent antimicrobial activity is obtained on the inside of gloves dipped into a starch slurry containing such antimicrobials, and this comprises one aspect of the invention, namely, a surgical glove having a layer of cross-linked starch on the inner surface thereof, wherein the starch has absorbed thereon an effective amount of an antimicrobial agent.

Salts of chlorhexidine, 1,6-di(4-chlorophenyl diguanido)hexane are bactericides which exhibit affinity for cross-linked cornstarch. These salts are adsorbed on the surface of cross-linked cornstarch and will release slowly therefrom in the presence of moisture such as perspiration. Typical salts of chlorhexidine are the dihydrochloride, dihydroiodide, diperchlorate, dinitrate, dinitrite, sulphate, sulphite, thiosulphate, di-acid phosphate, difluorophosphate, diformate, diacetate, dipropionate, di-isobutyrate, di-n-valerate, dicaproate, malonate, succinate, malate, tartrate, dimonoglycolate, monodiglycolate, dilactate, di-$\alpha$-hydroxyisobutyrate, digluconate, diglucoheptonate, di-isethionate, dibenzoate, dicinnamate, dimandelate, di-isophthalate, di-2-hydroxynapthoate, and embonate.

Another fmaily of antimicrobials that can be used in the invention are the biguanides or salts thereof such as polyhexamethylene biguanide hydrochloride ("PHMB"). PHMB is commercially available as COSMOCIL CQ from ICI Americas, Inc. The use of PHMB in the adhesive layer of an incise drape to render the drape antimicrobial is described by Brown in U.S. Pat. No. 4,643,181.

Chlorinated phenols of the type described in U.s. Pat. Nos. 2,919,200 and 3,308,488 to Dubin et al. and Schoonman, respectively, which are compounded into synthetic yarns to render the yarns antimicrobial, are anti-bacterial agents having a decomposition temperature above the curing temperature of the elastomers that can be used with relative safety in contact with human skin. Such chlorinated phenols kill disease producing microorganisms including bacteria and fungi. Specifically, the antibacterial agents disclosed by Dubin et al., i.e., 2,2'-thiobis(4,6-dichlorophenol) and 2,2'-methylenebis(3,4,6-trichloro)phenol may be employed. Even more preferably, because of its overall properties, an antimicrobial agent which can be utilized to fulfill the purposes of the invention is 2,4,4'-trichloro-2'-hydroxyphenyl ether, which has a USAN nonproprietary designation of triclosan. This material is marketed under the trade name "Irgasan DP-300" by the CIBA-GEIGY Corporation. Other antibacterial or fungicidal agents that are safe for use in contact with the skin may also be used. Such additional agents include nitrophenyl acetate, phenyl hydrazine, and polybrominated salicylanilides, such as 5,4'-dibromosalicylanilide and 3,5,4'-tribromosalicylanilide.

Several types of antimicrobials have been disclosed above which can be employed in the invention. The scope of the invention should not be limited to the specifically disclosed materials, but also includes their functional equivalents. Any antimicrobial that has low toxicity and low sensitization potential at effective use concentrations can be employed in the invention.

Because it is not the intent of the gloves of this invention to administer the active ingredient to the wearer of the glove, the inner coating is free of any additive materials that would tend to deliver the active ingredient to the wearer. The types of additive materials that are excluded include vehicles that would cause the active antimicrobial ingredient to pass through the skin of the wearer such that the active ingredient would be delivered systemically, and additive materials that would tend to enhance the adhesion or persistence of the active antimicrobial ingredient on the skin of the wearer. Preferably, the inner coating is free of all non-standard materials except for the antimicrobial agent. (By "non-standard" materials is meant materials that are not normally present on the inner surface of a medical glove.)

In another aspect of the invention, an antimicrobial may be incorporated in a surface layer on the gloves that are manufactured with powder-free processes, as discussed below. Surgical gloves made without powder on the inner surface must have that surface modified to allow donning. A method is described in U.S. Pat. Nos. 4,070,713 and 4,143,109. This approach necessitates the application of a low coefficient of friction ("C.O.F.") elastomeric coating to the inside of the gloves. These coatings can by any low C.O.F. plastic or elastomer with adequate adhesion to the natural rubber substrate and with physical stress/strain properties, i.e., tensile, modulus, and elongation compatible with the substrate, Elastomeric coatings applicable to this approach are carboxylated styrene butadiene latices, carboxylated butadiene acrylonitrile latices, sulfo-brominated butyl latices, polyurethane latices, vinyl acrylate latices, polyurethane solvent solutions, and several block copolymers as solvent solutions. Block copolymers which can be used include styrene/butadiene/styrene, styrene/isoprene/styrene and styrene/butylene/styrene. The examples given are not intended to limit or to suggest that only these elastomers can be used to fulfill the concept of this variation.

In the experimental section below, the antimicrobial activity of the particular variation of antimicrobial gloves was determined in the following manner. One tenth of a milliliter of each of the test suspensions of particular bacteria in 0.1 percent peptone growth medium were applied to the antimicrobial containing side of a two-inch square piece of the glove which had been placed in a petri dish. The glove had been presterilized in a sealed package by exposure to gamma radiation. The petri dish is then placed in a high humidity (95%) incubator at 35° C. for the particular exposure times. Controls, when used, were identical to the treated gloves except for the absence of the antimicrobial active ingredient. At the end of the exposure period, 20 mL of neutralizer solution was added to each petri dish containing a glove sample (2-inch square piece). The petri dishes containing the neutralizer were swirled in order to inactivate the antimicrobial and to remove the viable organisms from the surfaces of the glove samples. After 10 seconds of swirling, aliquots of the neutralizer medium were taken for enumeration of the viable organisms using the standard pour plate technique. (Reference: P. Gerhardt et al., MANUAL OF METHOD FOR GENERAL BACTERIOLOGY, Chapter 11, page 185, American Society for Microbiology, Washington, D.C., 1981.) The colonies were counted to determine the $\log^{10}$ for surviving bacteria after each exposure time.

EXAMPLE 1

Natural rubber surgical gloves were manufactured in a conventional manner. After the drying and curing ovens, the following mixture was dipped or sprayed on the glove as an aqueous slurry:

1.0 g of 50% active silicone emulsion LE-46HS
2.5 g of 20% chlorhexidine gluconate
8.0 g of a 50% slurry of epichlorohydrin cross-linked cornstarch The 50% cross-linked starch slurry contained 2.5 g of Gelvatol 20-60 polyvinyl alcohol and a total of 86 g of deionized water. The mixture is dipped or sprayed onto the warm gloves as they exit the ovens. After the mixture dries, the gloves are stripped from the forms. The gloves are reversed during stripping, which places the antimicrobial, starch powder, and silicone mixture on the inside of the gloves. Results of an evaluation of the bactericidal activity of the coated side of the glove are shown in Table I, below.

EXAMPLE 2

Natural rubber surgical gloves were manufactured in a conventional manner. A post dip of the following mixture was applied after the curing ovens, as described in Example 1: 1.0 g of 50% active silicone emulsion LE-46HS, 2.5 g of 20% active PHMB, and 8 g of a 50% slurry of cross-linked cornstarch. The 50% slurry of cross-linked cornstarch contained National 1142:140 cross-linked starch and 2.4 g of Gelvatol 20-60 polyvinyl alcohol in 86 g of deionized water. The latter was dipped onto the gloves. Results of the evaluation of the bactericidal properties of the coated glove are shown below in Table I.

EXAMPLE 3

Using conventional procedures for making surgical gloves, the natural rubber substrate is formed on the glove mold. After the gelled natural latex compound has been leached, and prior to drying and curing, the following solution is dipped over the substrate.

Dissolve 15 g of Estane 5707, polyurethane elastomer, in 20 g of tetrahydrofuran, 20 g of toluene, 25 g of 1,4-dioxane, and 20 g of N,N-dimethylformamide (DMF). To the resultant solution, blend in 2.25 g of aqueous 20% PHMB. Results of the antibacterial testing are displayed in Table I, below.

EXAMPLE 4

As a control, gloves were prepared as outlined in Example 1, omitting only the antimicrobial.

EXAMPLE 5

Gloves are dipped as described in Example 3. The following polyurethane latex compound is overdipped prior to the dry and cure ovens:

To 50 g of 30% cationic urethane latex Neorez XP-7058, add 1.5 g of 30% cetyl trimethyl ammonium bromide, 0.6 g of 20% chlorhexidine gluconate, and 2.36 g of cross-linked starch 1142:140. Results of the antibacterial testing are shown below in Table I.

EXAMPLE 6

Gloves are dipped as described in Example 3. The following hypalon latex compound is overdipped prior to the dry and cure ovens:

To 200 g of 50% HYP-605 latex (chlorosulfonated polyethylene), add 5 g of 40% amphoterge SB (an amphoteric surfactant), 6 g of 50% pentaerythritol solvent, 4.33 g of 60% zinc oxide, 3.63 g of 55% dipentamethylene thiuram hexasulfide, 30 g of 50% Vedoc VP-180 urethane powder (used as an encapsulated low C.O.F. donning powder), 20 g of 50% Witcobond XW modified epoxy resin film forming polymer, 3 g of 2,4,4'-trichloro-2'-hydroxydiphenyl ether (triclosan), 1.33 g of 38% EDTA, and 3.00 g of diethylene glycol solvent. Results of the antibacterial testing are shown below in Table I.

EXAMPLE 7

As a control for one of the powder-free concepts, gloves were dipped as described in Example 6, omitting only the antimicrobial. Results of the antibacterial testing are shown below in Table I.

TABLE I

BACTERIAL % KILL

| Example | Initial Count | Count/% Kill 10 Min. | 30 Min. |
|---|---|---|---|
| Example 1 | 160,000 | 0/100% | 0/100% |
| Example 2 | 140,000 | 0/100% | 0/100% |
| Example 3 | 130,000 | 15/99.988% | 0/100% |
| Example 4 Control | 180,000 | 120,000/33.3% | 130,000/27.8% |
| Example 5 | 140,000 | 85,000/39.3% | 36,000/74.3% |
| Example 6 | 200,000 | 61,000/61.88% | 5,100/96.81% |
| Example 7 Control | 160,000 | 120,000/25.0% | 16,000/90% |

The Example 7 control is most properly compared only with Example 6 (which used the same latex coating on the inner surface of the glove). Apparently, this latex coating itself has mild antimicrobial activity.

In order to determine the order of magnitude of the rate of release of the antimicrobial agent from the coating in the medical glove, the following experiments were performed:

By procedures analogous to those described above in Examples 3-7, surgical gloves having low C.O.F. coatings containing antimicrobial agents were coated with the following aqueous mixtures:

| Material | Example 8 Parts, by weight, dry | % Solids | Parts, by weight, wet |
|---|---|---|---|
| Deionized water | — | — | 206.535 |
| Witcobond W-212[1] | 100 | 29.6 | 337.84 |
| Chlorhexidine gluconate | 3 | 20.0 | 15.0 |
| Geon 213[2] | 15 | 50.0 | 30.0 |
| Amphoterge SB[3] | 0.125 | 10.0 | 1.25 |

| Material | Example 9 Parts, by weight, dry | % Solids | Parts, by weight, wet |
|---|---|---|---|
| Deionized water | — | — | 297.25 |
| Neorez R-967[4] | 30.0 | 40.0 | 75.0 |
| Neorez R-962[5] | 70.0 | 34.0 | 205.88 |
| Vedoc VP-180[6] | 17.65 | 50.0 | 35.3 |
| Triclosan | 6.0 | 100.0 | 6.0 |
| Propylene glycol | 6.0 | 100.0 | 6.0 |
| Versene 100[7] | 1.0 | 38.0 | 2.64 |

[1] An aqueous dispersion of fully reacted urethane polymer.
[2] A calender grade polyvinyl chloride resin
[3] A sulfonated amphoteric surfactant. CFTA adopted name is "Amphoteric 13". The Geon 213 and Amphoterge SB were pre-mixed prior to addition to the aqueous mixture.
[4] and [5] Colloidal dispersions of high molecular weight aliphatic urethane polymers
[6] An aqueous polyester urethane polymer powder mixture
[7] Na salt of EDTA The gloves prepared as described above in Examples 8 and 9 were tested for extraction of the antimicrobial agents in the following manner:

Fifty ml of physiological saline was placed in each sample glove. The gloves were hung in a 100° F. oven to simulate body temperature, and aliquots of saline were removed from each glove after 30 minutes and after 1, 2, and 4 hours. The removed samples were analyzed by a spectrophotometer for extracted antimicrobial agent. The results are reported below as ppm of extracted antimicrobial agent in the saline:

|  | Example 8 | Example 9 |
|---|---|---|
| 30 min. | 3.0 | <0.5 |
| 1 hr. | 3.1 | <0.5 |
| 2 hrs. | 4.6 | ~0.8–1.0 |
| 4 hrs. | 6.9 | ~0.8–1.0 |

What is claimed is:

1. An antimicrobial medical glove consisting essentially of an outer elastomeric body in the shape of a hand and an inner coating containing an antimicrobial agent, said inner coating being capable of slowly releasing said antimicrobial agent in an amount and over a period of time sufficient to maintain an essentially bacteria-free and fungus-free environment within said glove after said glove has been donned, wherein said inner coating comprises cross-linked starch, and wherein said antimicrobial agent is selected from the group consisting of chlorhexidine, or salts thereof, biguanides or salts thereof, chlorinated phenols, nitrophenyl acetate, phenyl hydrazine, and polybrominated salicylanilides.

2. The medical glove of claim 1 wherein the antimicrobial agent is chlorhexidine or salt thereof.

3. The medical glove of claim 2 wherein the salt of chlorhexidine is chlorhexidine gluconate.

4. The medical glove of claim 1 wherein the antimicrobial agent is polyhexamethylene biguanide or salt thereof.

* * * * *